United States Patent
Armstrong et al.

(10) Patent No.: US 6,733,986 B1
(45) Date of Patent: May 11, 2004

(54) METHOD AND AGENT FOR DETERMINING A DEAMINASE ENZYMATIC ACTIVITY

(75) Inventors: Lyle Armstrong, Newcastle (GB); Arthur James, Newcastle (GB); Sylvain Orenga, Neuville (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/530,518

(22) PCT Filed: Nov. 6, 1998

(86) PCT No.: PCT/FR98/02380

§ 371 (c)(1),
(2), (4) Date: May 25, 2000

(87) PCT Pub. No.: WO99/24604

PCT Pub. Date: May 20, 1999

(30) Foreign Application Priority Data

Nov. 6, 1997 (FR) .............................. 97 14191

(51) Int. Cl.[7] ................................... C12Q 1/04
(52) U.S. Cl. ..................... 435/34; 435/16; 435/29
(58) Field of Search ................. 435/34, 16, 29

(56) References Cited

U.S. PATENT DOCUMENTS

| | | | | |
|---|---|---|---|---|
| 3,725,203 A | * | 4/1973 | Sellers | |
| 4,507,230 A | * | 3/1985 | Tam et al. | |
| 4,603,108 A | | 7/1986 | Bascomb | |
| 4,937,352 A | * | 6/1990 | Voelter | |
| 5,173,434 A | * | 12/1992 | Morris et al. | |
| 5,411,867 A | | 5/1995 | Change et al. | |
| 5,541,082 A | | 7/1996 | Bochner | |
| 5,643,743 A | | 7/1997 | Chang et al. | |
| 5,668,254 A | * | 9/1997 | Denghenghi | |

FOREIGN PATENT DOCUMENTS

| EP | 0 424 293 A1 | 4/1991 |
| WO | WO 92/00068 | 1/1992 |

OTHER PUBLICATIONS

Derwent abstract (Acc. No. 1986–028300) of EP 171158A (1986). Beggs et al. Detection of tryptophan–deaminase positive microorganisms—by measuring fluorescence after exposure to fluorophore and chromogenic metal ions.*

Giammanco G. & Pignato S.: "Rapid identification of micro–organisms from urinary tract infections by beta–glucuronidase, phenylalanine deaminase, cytochrome oxidase and indole tests on isolation media", Journal of Medical Microbiology, vol. 41, No. 6, pp. 389–392.

Manafi M. & Rotter "A new plate medium for rapid presumptive identification and differentiation of Enterobacteriaceae", International Journal of Food Microbiology, Vol 14, No 2, pp. 127–134.

Chemical Abstract Vol 96, No. 19 Abstract No. 158923, Sivolodskii, E.P.; "Modification of a method for the determinationo f tryptophan deaminase and phenylalanine deaminase content in bacteria,"No. 3, 1982, pp. 166–168.

Chemical Abstract Vol 78, No. 5, Abstract No 26194, Peloux &. & Lefort, H. "Lysine deaminase of the Proteus–Providencia group by means of the Edwards and Fiflysine–iron medium. Practical value of this medium for differentiating enterobacteria."XP002073587.

* cited by examiner

Primary Examiner—Ralph Gitomer
(74) Attorney, Agent, or Firm—Oliff & Berridge, PLC

(57) ABSTRACT

A method and compound for detecting and identifying and/or quantifying a deaminase enzymatic activity of a microorganism, according to which an inoculum suspected of containing a microorganism with a deaminase activity is brought into contact with a culture medium for microorganisms, wherein the culture medium comprises at least one detection agent for demonstrating, by forming a colored product with a revealing agent, a deaminase enzymatic activity;

said detection agent being an L-amino acid of following general formula (I):

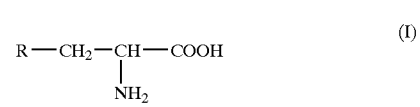

in which R represents an organic radical containing a cyclic ring, said cyclic ring being substituted with 1 to 3 substituents that are identical or different and each of which limits the diffusion in the culture medium of the α-keto acid produced by the deamination of the at least one detection agent, as compared to where each of said substituents is not present.

29 Claims, No Drawings

METHOD AND AGENT FOR DETERMINING A DEAMINASE ENZYMATIC ACTIVITY

This application claims priority to application PCT/FR98/02380 filed Nov. 6, 1998 which claims priority to France 97 14191 filed Nov. 6, 1997.

The present invention relates to a method for detecting and identifying and/or quantifying an enzymatic activity such as deaminase activity in a culture medium for microorganisms, to the compounds and detection agents which are suitable for this method, to the method for preparing these compounds and detection agents, as well as to the culture media for implementing said method.

The detection and identification of microorganisms are very important in particular in medicine, in the agrifoods industry or for environmental control (water, etc.). Microorganisms may be sought for their pathogenicity, as contamination indicators, for monitoring manufacturing methods, and the like.

The techniques for detecting and identifying microorganisms are currently based on the search for characteristic nucleotide sequences, the search for antigens or antibodies, culturing in selective or nonselective medium, or alternatively the search for metabolic and in particular enzymatic activities (for example osidase, esterase, peptidase, oxidase, etc. activities).

Usually, the methods for detecting and identifying and/or quantifying microorganisms combine several of these techniques. Culturing is thus used to multiply and select the desired microorganisms. In order to simply their detection, it has been proposed to demonstrate biochemical activities by introducing molecules which produce a coloration or a fluorescence, directly into the culture medium. Such media are referred to as detection media. The biochemical activities can be demonstrated by various methods, such as:

- physicochemical modification of the medium: change in pH in the presence of a colored or fluorescent indicator (methylumbelliferone, etc.),
- change in the redox potential, revealed with the aid of a colored indicator (tetrazolium salts, etc.) or a fluorescent indicator (EPO-424 293),
- hydrolysis of molecules which release a colored compound or a fluorescent compound (indoxyl, naphthol, coumarin, etc.),
- reaction of a molecule which is produced by the microorganisms with a compound which is present in the medium and which results in a coloration (detection of indole, James et al., 1986).

It is known that gelled (or solid) media are particularly suitable for culturing and isolating microorganisms from a sample, as well as for detecting "target" microorganisms in a mixture of microorganism taxa.

A method for differentiating bacteria of the Proteus group from other enterobacteria is known (Sverre Dick Henriksen, State Institute for Public Health, Bacteriological Department, Oslo, Norway, Jun. 6 1950). This method uses an equal amount, in gelled medium, of D- and L-phenylalanine in the presence of iron salt. In comparison with the urease assay, the green colored reaction obtained, although positive for identifying the Proteus group, is presented as being an assay which is laborious to use.

The document by GIAMMANCO & PIGNATO ("Rapid identification of microorganisms from urinary tract infections by beta-glucuronidase, phenylalanine deaminase, cytochrome oxidase and indole tests on isolation media", JOURNAL OF MEDICAL MICROBIOLOGY, vol. 41, No. 6, December 1994, pages 389–392) is also known, which discloses, for detecting a deaminase activity of bacteria of the Proteeae group, the use of natural amino acids, such as tryptophan and phenylalanine, in combination with an iron salt ($FeCl_3$).

The document by MANAFI & ROTTER ("A new plate medium for rapid presumptive identification and differentiation of Enterobacteriaceae", INTERNATIONAL JOURNAL OF FOOD MICROBIOLOGY, vol. 14, No. 2, November 1991, pages 127–134) is also known, which discloses, for detecting a deaminase activity of bacteria of the Proteeae group, the use of tryptophan alone with iron salt (ammoniacal iron citrate). This document mentions, for other markers of enzymatic activity (4-methylumbelliferone, nitrophenyl), that a diffusion of these markers is detrimental. The only solution for minimizing the effect thereof is to incubate the media for a shorter time.

The document by PELOUX & LEFORT ("Lysine deaminase of the Proteus-Providencia group by means of the Edwards and Fife lysine-iron medium. Practical value of this medium for differentiating enterobacteria", FEUILL. BIOL., vol. 13, No. 68, 1972, pages 37–42) is also known, which compares the activity of three amino acids (tryptophan, phenylalanine and lysine), for detecting deaminase, in combination with an iron salt.

The document by SIVOLODSKII ("Modification of a method for the determination of tryptophan deaminase and phenylalanine deaminase content in bacteria", LAB. DELO., No. 3, 1982, pages 166–168) is also known, which proposes adding enzymatic hydrolysates of proteins, consisting of mixtures of natural amino acids, of peptides and of other compounds, in order to detect tryptophan and phenylalanine deaminase activities.

Patent application WO-A-92/00068 is also known, which discloses substituted histidine compounds which act as antagonists of angiotensin II receptors. These compounds, according to the formula (I) and the examples, comprise, inter alia, the substitution of the amine or carboxyl group.

U.S. Pat. Nos. 5,643,743 and 5,411,867 are also known, which disclose tryptophan for detecting tryptophanase, this enzyme being different from the deaminases.

U.S. Pat. No. 4,603,108 is also known, which discloses D,L-beta(p-nitrophenyl)alanine as a substrate for detecting phenylalanine deaminase. The reading of the reaction is carried out either at 480 nm, without adding a revelator, for phenylalanine deaminase, or by assaying ammonia for leucine deaminase.

Finally, U.S. Pat. No. 5,541,802 is known, which discloses, for detecting deaminases, the amino acids phenylalanine and tryptophan, which make it possible to obtain an orangey color which diffuses in the medium.

Either these documents disclose the use of natural amino acids, which is incompatible with a limitation of the diffusion of alpha-keto acid. The only solution proposed by certain of these documents comes down to limiting the incubation time, which is very prejudicial to the quality of the detection. However, the limitation of diffusion is evidence of differentiation of several microbial colonies present in the same medium. Or these documents disclose the use of artificial and modified amino acids which do not satisfy formula (I) of the invention, and which can, in addition, provide a different application, such as for example antagonism with angiotensin II receptors.

Despite all the biochemical assays currently on the market, it turns out that currently there are no means available, which are particularly well-suited and easy to implement, in particular in gelled medium, for detecting and identifying and/or quantifying, in a multimicrobial culture, an enzymatic activity such as a deaminase activity of microorganisms.

The present invention thus intends to resolve this problem.

A first subject of the invention is a method for detecting and identifying and/or quantifying an enzymatic activity such as deaminase activity of a microorganism, according to which an inoculum which is capable of containing a microorganism with a deaminase activity is brought into contact with a culture medium for microorganisms, the culture medium comprising at least one detection agent for demonstrating, by forming a colored product with a revealing agent, an enzymatic activity such as deaminase activity; said detection agent is a cyclic L-amino acid of following general formula (I):

in which:
R represents a cyclic amino acid radical, substituted with 1 to 3 groups X, which are identical or different,
X represents a group which limits the diffusion of the α-keto acid produced by the deamination of the cyclic amino acid,
the compound of formula (I) being able to be substituted with various groups which do not interfere with the function of the group X.

"Group which limits the diffusion" is intended to mean:
any group of hydrophobic type which limits the diffusion in a hydrophilic medium, or
any group which makes it possible to associate with, via weak bonds, in particular hydrophobic bonds, or to bind to, via one or more covalent bonds, in particular thiol bonds, constituents of the cells of the microorganisms, such as the wall, the membrane, the proteins, etc.

As an assay defining the groups which limit the diffusion, a cyclic L-amino acid and a corresponding detection agent according to the invention are respectively inoculated, as a spot, at the center of two Petri dishes. The diameters of the diffusion of the α-keto acids produced by the enzymatic activity such as the deaminase activity of the inoculant are measured. The diameter of diffusion of the detection agent according to the invention should be less than that of the cyclic L-amino acid; it will then be considered that the detection agent limits the diffusion of the a-keto acid produced by the deamination of the L-amino acid.

"Cyclic amino acid radical R" is intended to mean cyclic or heterocyclic radicals R such as indole, phenyl, hydroxyphenyl and imidazole, which can undergo a reaction of substitution with the group X. These amino acids include amino acids which are natural or synthetic, or modified, in particular by substitution.

"Group which does not interfere with the function of the group X" is intended to mean any group which does not prevent the group X from limiting the diffusion of the α-keto-acid.

In addition, as used herein, the term "substituent" does not include hydrogen.

In the method according to the invention, adding at least one detection agent in suitable concentrations does not inhibit the multiplication of microorganisms in the appropriate culture media. The detection agent can thus be used by adding it to the culture medium of the microorganisms before the start of the culture or at the start of culture.

One of the important advantages of the method using detection agents according to the invention is that in the presence of an enzymatic activity such as deaminase activity, it gives, after adding a revealing agent, colored products which do not diffuse in the medium, in particular in a gelled medium.

The method according to the invention can thus advantageously be used in gelled medium. It can also, of course, be used in liquid medium or on a solid support in the absence of gelling agent.

The method according to the invention makes it possible, in a multimicrobial medium, to detect and identify, or even quantify microorganisms with an enzymatic activity such as deaminase activity, and to do so without interfering with the detection of other microorganisms. On the contrary, the method according to the invention makes it possible, with the set of enzymatic reactions produced, to reveal distinctly, with colors which define the type of microorganism, the microorganism(s) present in the medium.

The method according to the invention thus provides the advantage, besides that of detecting and identifying an enzymatic activity such as deaminase activity in a culture medium, of allowing a simple and inexpensive implementation.

In a preferential embodiment according to the invention, the revealing agent is a cation salt.

The cation salt, which makes it possible to reveal the detection agent by forming a colored product, can be added to the culture medium at the same time as the detection agent, or indeed after culturing the microorganisms. In fact, persons skilled in the art will know how to determine, according to the culture medium used, whether it is more advantageous, or whether it is preferable, to add the cation salt at the same time as the detection agent or after culturing the microorganisms. However, adding the revealing agent to the culture medium at the same time as the detection agent is preferred, in particular in gelled medium.

The reaction which takes place between the detection agent and the deaminase, and then the revealing agent, in the presence of flavoprotein, when for example phenylalanine is used as a detection agent is the following general reaction:

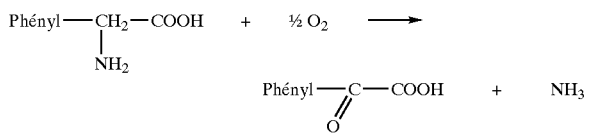

The phenylpyruvic acid obtained, which is an alpha-keto acid, combines with iron chloride, which acts as a chelating agent, to give a green coloration. Thus, when a tube containing such a composition is exposed to atmospheric oxygen, the coloration density increases.

According to the nature of the amino acid used, the final color obtained varies. For example, in the case of histidine, the coloration is brown.

This reaction is respected when the phenyl group is replaced with another ring and is substituted one to three times with a group X according to the formula (I).

The microorganisms which are detected and identified and/or quantified by enzymatic activity such as deaminase activity according to the method of the invention belong, in particular, to the group Proteus.

In a very preferential embodiment according to the invention, at least one other detection agent for demonstrating, by forming a colored or fluorescent product, an enzymatic activity which is different from that demonstrated by the compound of general formula (I), is also added to said culture medium. It can be for example an esterase, oxidase or peptidase activity. Additional information can also be obtained, in connection with an absence of coloration (or of fluorescence) or in connection with a coloration which is modified with respect to the coloration obtained with a single enzymatic substrate. The other detection agent chosen will have properties which are different from those of the detection agents of formula (I) according to the invention. For example, another detection agent which is capable of giving a reaction product with a color which is different from the color obtained with the detection agents of formula (I) will be chosen. The other detection agent (or second detection agent) will thus make it possible to reveal, due to its own color or due to its fluorescence, the presence of an enzymatic activity for which it is specific. If the enzymatic activity such as deaminase activity, which is detectable by the detection agent [sic] of formula (I) according to the invention, is also present, and can be revealed with a characteristic color, a modified coloration, which is different from said characteristic color and which is also different from said own color given by the second detection agent, will be obtained. Examples of using several detection agents in the same culture medium are given in the following examples. Obviously, the results can vary with the choice of the detection agent according to the invention which is used, the second (or more) detection agent used and the various microorganisms present in the culture medium.

The other detection agents which are used to demonstrate different enzymatic activities are in particular, but not exclusively, indoxyl, coumarin, resorufin, naphthol, naphthylamine, nitrophenol, nitroaniline, rhodamine, hydroxyquinoline, fluorescein, etc. derivatives.

Among these other detection agents which can be used in combination with the detection agents according to the invention, mention may be made in particular of 5-bromo-4-chloro-3-indolyl-β-D-glucuronide, 6-chloro-3-indolyl-β-D-glucoside, L-alanine-7-amino-4-methyl-coumarin, 4-methylumbelliferyl-N-acetyl-β-D-galactos-aminide, resorufin-β-D-galactoside, β-naphthyl sulfate, naphthol AS-BI β-D-galactoside, L-alanine β-naphthyl-amide, O-nitrophenol-β-D-galactoside, carboxybenzoyl-L-arginine-p-nitroanilide, rhodamine 110 bis-(L-leucine amide) and fluorescein diacetate.

A second subject of the invention are the compounds having the following general formula (I):

(I)

in which:
R represents a cyclic amino acid radical, substituted with 1 to 3 groups X, which are identical or different,
X represents a group which limits the diffusion of the α-keto acid produced by the deamination of the cyclic amino acid,
the compound of formula (I) being able to be substituted with various groups which do not interfere with the function of the group X, with the exception of the compounds N-im-benzyl-L-histidine, 1- and 3-methyl-L-histidine, O-benzyl-L-tyrosine, O-carboxybenzoyl-L-tyrosine, O-dansyl-L-tyrosine, O-methyl-L-tyrosine and 1-, 4-, 5-, 6- and 7-methyl-L-tryptophan.

The abbreviations "N-im" for an L-histidine compound, and "N-im" for an L-tryptophan compound signify that the nitrogen atom of the imidazole nucleus (His) or the nitrogen atom of the indole nucleus (Trp) is substituted.

A third subject according to the invention is a detection agent comprising at least one compound of following general formula (I):

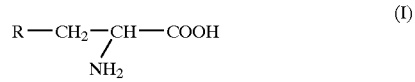
(I)

in which
R represents a cyclic amino acid radical, substituted with 1 to 3 groups X, which are identical or different,
X represents a group which limits the diffusion of the α-keto acid produced by the deamination of the cyclic amino acid, the compound of formula (I) being able to be substituted with various groups which do not interfere with the function of the group X.

In a preferential embodiment, the detection agent comprises at least one compound of following general formula (I):

(I)

in which R is substituted with a group X, and X is chosen from hydrophobic groups.

In an even more preferred embodiment, the detection agent comprises at least one compound of following general formula (I):

(I)

in which R is substituted with a group X, and X is chosen from methyl, benzyl, carboxybenzoyl, dansyl, naphthalene-sulfonyl, toluene-sulfonyl and mesitylene-sulfonyl.

A fourth subject according to the invention is the method for preparing compounds and detection agents according to the invention of general formula (I) and as respectively defined above, comprising the following steps:
(a)—formylation of the residue R,
(b)—addition of a salt of X onto the residue R formylated according to (a),
(c)—deformylation of the residue R substituted according to (b).

A fifth subject according to the invention is a culture medium for microorganisms comprising, besides the ingredients required for culturing said microorganisms, at least one detection agent as defined above.

The detection agents of cyclic X-L-amino acid formula are used at weight concentrations which are sufficient to give observable colored reactions. These concentrations can be determined by routine experiments by persons skilled in the art.

In a preferential embodiment, the weight concentration of the detection agent(s) in the culture medium is between 0.025 and 5 g/l of culture medium.

In a very preferential embodiment, the weight concentration of the detection agent(s) in the culture medium is between 0.1 and 2 g/l, preferably between 0.3 and 0.6 g/l.

In another preferential embodiment, the culture medium also comprises a revealing agent, preferably a cation salt, for example ammoniacal iron citrate. The concentration of the revealing agent is not limiting; it can be lower than, equal to, or higher than that of the detection agent of formula (I).

In another preferential embodiment according to the invention, the culture medium is in a gelled form.

In a very preferential embodiment according to the invention, the culture medium also comprises at least one other detection agent for demonstrating, by forming a colored or fluorescent product, an enzymatic activity which is different from that demonstrated by the compound of general formula (I).

As an example of a gelled medium, O-toluene-sulfonyl-L-tyrosine at 0.5 g/l and iron citrate at 0.5 g/l can be incorporated into the culture medium, in the following medium:

| Heart-brain extract | 5 g/l |
| bio-Soyase | 5 g/l |
| Tris buffer | 1 g/l |
| Monopotassium phosphate | 1 g/l |
| Agar | 17.5 g/l, | this medium being able to be inoculated with various Gram-negative or Gram-positive microorganisms. Only the strains which belong to the group Proteus form brown colonies after 18 to 24 hours of incubation. The strains which do not belong to the group Proteus form colonies which conserve the appearance that they have on the same medium lacking in O-toluene-sulfonyl-L-tyrosine.

The properties and advantages of the invention are illustrated with the following examples.

EXAMPLE 1

Synthesis of 2-O-naphthalene-sulfonyl-L-tyrosine

Synthesis of N-formyl-L-tyrosine.

L-Tyrosine (60 g; 0.33 mol) was dissolved in 98% formic acid (400 ml) and cooled to 10° C. Acetic anhydride, (192 ml; 1.73 mol) was added in four stages for five minutes, while at the same time maintaining a temperature of 10° C. The mixture was then stirred for 60 min at 10° C. and then kept at room temperature for 30 min. Water (192 ml) was added with stirring at 10 to 15° C. for 30 min, and then the mixture was subjected to evaporation under reduced pressure at 70° C., until a dry residue was obtained. The residual oily solid was dissolved in a minimal volume of boiling water, and then cooled to produce fine white crystals of N-formyl-L-tyrosine (60.6 g; 88%).

Synthesis of N-formyl-O-(2-naphthalene-sulfonyl)-tyrosine.

Method A

The N-formyl-L-tyrosine (14.0 g; 0.0668 mol) was dissolved in acetone (250 ml) and the solution was diluted with water (190 ml). The pH was adjusted to 9.7 by addition of saturated sodium carbonate solution, and a solution of naphthalene-2-sulfonyl chloride (15 g; 0.0668 mol) in acetone (42 ml) was then added dropwise for 20 min at room temperature, while at the same time maintaining the pH at 9.7 by the addition of sodium carbonate solution. The mixture was stirred for 60 min and left to stand for 12 hours, after which the acetone was largely evaporated off under a reduced pressure at 50° C. The residual solution was cooled to 5° C. and then extracted with ether (2×50 ml). The aqueous phase was then acidified until a pH of 3.5 was obtained, producing a dense white precipitate, which was recovered by filtration, and dried in an oven under vacuum at 60° C. to give a white solid (24.57 g; 92%).

Deformylation

The N-formyl-O-(2-naphthalene-sulfonyl)-tyrosine (24.57 g; 0.0615 mol) was resuspended in acetone (105 ml) and added in small amount to a refluxing mixture of concentrated hydrochloric acid (240 ml) and water (240 ml). The mixture was heated under reflux for 3 hours and was then poured into water (750 ml) with stirring and cooling to 10° C. The pH was adjusted to 3.5, and the resulting dense white precipitate was recovered by filtration, and dried in an oven under vacuum at 50° C. to give a clean white powder (21.25 g; 94%). The product might be further purified with a solution of aqueous sodium hydroxide and the addition of acid. The yield of the dry product was 79%.

The total yield obtained from L-tyrosine is 64%.

EXAMPLE 2

Synthesis of 4-O-tosyl-L-tyrosine

The synthesis of 4-O-toluene-sulfonyl-L-tyrosine was carried out according to two methods below:

Method A

The compound was prepared in accordance with the method described in Example 1, but substituting the naphthalene-2-sulfonyl chloride with the molar equivalent of toluene-sulfonyl chloride. The total yield of product was 56%.

Method B

Copper sulfate pentahydrate (5 g; 20 mmol) was dissolved in water (100 ml) with stirring, and a solution of potassium hydroxide (2.25 g; 40 mmol) in water was added continuously. After 15 min, the suspension was left to stand and filtered, and the residue was washed with a small amount of water and then partially dried to produce a "blue residue".

The L-tyrosine (7.2 g; 40 mmol) was resuspended in water (100 ml) and aqueous potassium hydroxide (3.36 g; 60 mmol) was added. Copper hydroxide prepared above was added to this hot solution. The resulting dark blue solution of the copper complex was carefully acidified down to pH 8. The purple precipitate which progressively formed was isolated by filtration, washed with water and methanol, and air-dried to give 7.4 g of complex. This complex was resuspended in methanol (80 ml), and to a solution of sodium carbonate (3.7 g; 35 mmol) was added with stirring. The copper complex, which was only dissolved, required the use of methanol to clarify it. A solution of 4-toluene-sulfonyl chloride (6.55 g; 35 mmol) in methanol (60 ml) was gradually added to the stirred filtered solution. The pH was maintained between 9 and 11 by the periodic addition of aqueous sodium carbonate. After 2 hours, the suspension was filtered, and the residue was washed with methanol. The washing and filtration steps were combined, and the suspension was subjected to evaporation at 45° C. to remove the methanol.

The resulting blue solid was decomposed by vigorous stirring with hydrochloric acid (15 ml) and ice (30 g). The light green solid was removed and dissolved directly in hot water (100 to 120 ml). A cooling and an adjustment of the pH to 7.5 produced a large amount of white precipitate. This precipitate was removed by filtration. The residue was redissolved in a similar volume of hot water containing EDTA (300 mg), to remove the traces of cupric ions, and the pH was again adjusted to 7.5. The product was isolated in the form of a silvery white solid, after filtration and drying (6.1 g; 52%).

EXAMPLE 3

Synthesis of O-mesitoyl-L-tyrosine

N-a-t-BOC-L-Tyrosine (2.81 g; 10 mmol) was dissolved in pyridine anhydride [sic] (15 ml). 2,4,6-Trimethylbenzoyl chloride (1.92 g; 10.5 mmol) was slowly added to this solution. The temperature was maintained between 15° C. and 25° C. After stirring for 30 min, the reaction mixture was poured onto ice water. The sticky solid was subjected to an extraction into dichloromethane (2×50 ml), and the organic layer was washed with water (3×50 ml) and dried on anhydrous magnesium sulfate. The evaporation of the solvent led to the production of a vitreous solid which slowly crystallized.

The product was deprotected by dissolving it in a small amount of ethyl acetate, and by addition of a solution of hydrogen chloride (3M) in ethyl acetate (5 ml). The stirred solution gradually formed a deposit in the form of a white solid. A maximum precipitation was obtained by the addition of diethyl ether (30 ml).

The product was removed by filtration under vacuum, washed with ether and dried in a desiccator under vacuum (2.5 g; 69%).

EXAMPLE 4

Synthesis of N-in-mesitylene-2-sulfonyl-L-tryptophan

N-a-t-BOC-N-in-Mesitylene-2-sulfonyl-L-tryptophan (1.0 g; 1.5 mmol) was suspended in ethyl acetate (5 ml), and a solution of hydrogen chloride (3 M) in ethyl acetate (2.5 ml) was added to the stirred solution. A white precipitate rapidly formed and intensified with the stirring. After 2 hours, the suspension was filtered, and the residue was washed with ether, dried and stored. Although thin layer chromatography showed only one component (under ultraviolet visualization), the product was probably contaminated with dicyclohexylammonium chloride. No attempt was made to remove this contaminant, and the product was used as it is for testing. The yield was 0.68 g.

EXAMPLE 5

Synthesis of N-im-(4-toluene-sulfonyl)-L-histidine

N-a-t-BOC-N-im-Tosyl-L-histidine (1.0 g; 2.44 mmol) was dissolved in a solution of hydrogen chloride (3 M) in ethyl acetate (5 ml). After stirring for 2 hours, the compound was isolated in the form of a hydrochloride salt as described in Example 4 and gave a white solid (0.64 g; 76%).

Similarly, O-(2,6-dichlorobenzyl)-L-tyrosine, N-im-benzyloxycarbonyl-L-histidine and Np-benzyloxy-methyl-L-histidine were prepared by intermediate protections, which are commercially available for peptide synthesis.

Tests were carried out to illustrate the advantage of the compounds of formula (I) according to the invention for detecting bacteria of the genus Proteus on gelled media.

EXAMPLE 6

Two media were prepared according to the usual techniques. They had the same composition, with the exception of the detection agent used for demonstrating the enzymatic activity such as deaminase activity.

The composition of the Media I and II for one liter of final medium is as follows:

| | |
|---|---|
| Heart-brain extract (bioMérieux) | 5 g/l |
| bio-Soyase (bioMérieux) | 5 g/l |
| Tris buffer (Prolabo) | 1 g/l |
| Monopotassium phosphate (Merck) | 1 g/l |
| Agar (bioMérieux) | 17.5 g/l |
| Ammoniacal iron citrate (Sigma) | 0.5 g/l |

The pH of the media was adjusted to approximately 7.2.

In the Medium I, the detection agent for enzymatic activity such as deaminase activity which is used is the natural amino acid L-tyrosine, at 1.5 g/l; in Medium II, the detection agent for enzymatic activity such as deaminase activity which is used is 4-O-toluene-sulfonyl-L-tyrosine, at 0.5 g/l.

12 bacterial strains were cultured directly in Petri dishes, on these two media. The strains which originate from the applicant's collection belong to the following species: *Escherichia coli* (2 strains), *Enterobacter cloacae* (1 strain), *Klebsiella pneumoniae* (1 strain), *Morganella morganii* (2 strains), *Proteus mirabilis* (2 strains), *Proteus vulgaris* (2 strains), *Enterococcus faecalis* (1 strain), *Staphylococcus saprophyticus* (1 strain). In addition, a mixture of one *E. coli* strain and of one *P. mirabilis* strain was also cultured in Petri dishes. The dishes were incubated at 37° C. for 48 hours. The colonies formed were examined visually, after respectively 24 and 48 hours of incubation, according to the following interpretations:

- the brown colonies correspond to strains which produce a deaminase belonging a priori to the group Proteus (represented herein by the species: *M. morganii, P. mirabilis, P. vulgaris*);
- the white colonies correspond to the strains which do not produce the abovementioned enzyme; they thus belong to other bacterial species which are therefore to be identified with the aid of the usual techniques;
- the diffusion of the brown precipitate around the colony is assessed according to a semi-quantitative scale (nil, weak, strong).

The results are presented in Table I below:

TABLE I

| | | at 24 hours | | | | at 48 hours | | | |
|---|---|---|---|---|---|---|---|---|---|
| | | Colonies | Diffusion | | | Colonies | Diffusion | | |
| Species | Medium | Brown | Nil | Weak | Strong | Brown | Nil | Weak | Strong |
| E. coli | I | —* | — | — | — | — | — | — | — |
| (2 strains) | II | — | — | — | — | — | — | — | — |
| E. cloacae | I | — | — | — | — | — | — | — | — |

TABLE I-continued

|  |  | at 24 hours | | | | at 48 hours | | | |
|  |  | Colonies | Diffusion | | | Colonies | Diffusion | | |
| Species | Medium | Brown | Nil | Weak | Strong | Brown | Nil | Weak | Strong |
| (1 strain) | II | — | — | — | — | — | — | — | — |
| K. pneumoniae | I | — | — | — | — | 1 | — | 1 | — |
| (1 strain) | II | — | — | — | — | — | — | — | — |
| M. marganii | I | 2 | — | — | 2 | 2 | — | — | 2 |
| (2 strains) | II | 2 | 2 | — | — | 2 | 2 | — | — |
| P. mirabilis | I | 2 | — | — | 2 | 2 | — | — | 2 |
| (2 strains) | II | 2 | 2 | — | — | 2 | 2 | — | — |
| P. vulgaris | I | 2 | — | — | 2 | 2 | — | — | 2 |
| (2 strains) | II | 2 | 2 | — | — | 2 | 2 | — | — |
| E. faecalis | I | — | — | — | — | — | — | — | — |
| (1 strain) | II | — | — | — | — | — | — | — | — |
| S. saprophyticus | I | — | — | — | — | — | — | — | — |
| (1 strain) | II | — | — | — | — | — | — | — | — |

*: number of strains, "—" = 0

As emerges from Table I above, the method according to the invention allows detection of bacteria of the group Proteus. Specifically, for the culture on Medium I, only one type of translucent-brown colony is found, on a background of orangey medium, whereas on the Medium II according to the invention, two types of colony emerge: one brown and the other translucent on a background of colorless medium, which is brown in the vicinity of the colored colonies.

EXAMPLE 7

Although the method according to the invention is more advantageously suitable for detecting an enzymatic activity such as deaminase activity in gelled medium or on a solid support, it can also be used in liquid medium.

Two media were prepared according to the usual techniques. They have the same composition, with the exception of the detection agent used for revealing the enzymatic activity such as deaminase activity.

The composition of the Media III and IV for one liter of final medium is as follows:

| Heart-brain extract (bioMérieux) | 5 g/l |
| bio-Soyase (bioMérieux) | 5 g/l |
| Tris buffer (Sigma) | 1 g/l |
| Monopotassium phosphate (Merck) | 1 g/l |
| Ammoniacal iron citrate (Sigma) | 0.5 g/l |

The pH of the media was adjusted to approximately 7.2.

In Medium III, the detection agent for the enzymatic activity such as deaminase activity which was used is the natural amino acid L-histidine, at 1.5 g/l; in Medium IV, the detection agent for the enzymatic activity such as deaminase activity which is used is of [sic] N-toluene-sulfonyl-L-histidine, at 0.5 g/l. The media were distributed into test tubes, in a sterile manner.

These two media were inoculated with the 12 bacterial strains described in Example 6. The tubes were incubated for 48 hours at 37° C., and were examined visually after 48 hours according to the following interpretation:

the browning of the tube reflects the presence of an enzymatic activity such as deaminase activity, and thus of a bacterium of the group Proteus, the absence of browning signifies the absence of bacteria of the group Proteus.

The results are presented in Table II below:

TABLE II

|  |  | Browning of the medium at 48 hours | | |
| Species | Medium | Strong | Weak | Nil |
| E. coli | III | — | 2 | — |
| (2 strains) | IV | — | — | 2 |
| E. cloacae | III | — | 1 | — |
| (1 strain) | IV | — | — | 1 |
| K. pneumoniae | III | — | 1 | — |
| (1 strain) | IV | — | — | 1 |
| M. morganii | III | 1 | 1 | — |
| (2 strains) | IV | 2 | — | — |
| P. mirabilis | III | 2 | — | — |
| (2 strains) | IV | 2 | — | — |
| P. vulgaris | III | 2 | — | — |
| (2 strains) | IV | 2 | — | — |
| E. faecalis | III | 1 | — | — |
| (1 strain) | IV | — | — | 1 |
| S. saprophyticus | III | — | — | 1 |
| (1 strain) | IV | — | — | 1 | number of strains, "—" = 0

As emerges from Table II above, in liquid medium, the detection agent according to the invention makes it possible, as does L-histidine, to differentiate the bacteria belonging to the group Proteus from those not belonging thereto, with a high sensitivity and specificity, after 48 hours.

EXAMPLE 8

Tests were also undertaken to test the possibility of simultaneously detecting an enzymatic activity such as deaminase activity according to the invention, as well as another enzymatic activity.

For this, three media were prepared according to the usual techniques. The first (Medium V), corresponds to Medium II of Example 6, in which the 4-O-toluene-sulfonyl-L-tyrosine was replaced with 4-O-dansyl-L-tyrosine at the same concentration, the second (Medium VI), corresponds to this same medium, but with 5-bromo-4-chloro-3-indolyl-β-D-glucoside at 0.1 g/l in place of the deaminase substrate, and the third (Medium VII), corresponds to Medium VI, to which 4-O-dansyl-L-tyrosine at 0.5 g/l is added.

The 12 bacterial strains described in Example 6 were cultured directly in Petri dishes, on these three media. In addition, a mixture of one strain of K. pneumoniae and of one strain of P. mirabilis was also cultured in Petri dishes. The dishes were incubated at 37° C. for 24 hours. The colonies formed were examined visually, after 24 hours of incubation, according to the following interpretations:

the brown colonies correspond to strains which produce a deaminase belonging a priori to the group Proteus (represented herein by the species: M. morganii, P. mirabilis, P. vulgaris);

the blue colonies correspond to the strains which express a β-D-glucosidase activity, and which hydrolyze 5-bromo-4-chloro-3-indolyl-β-D-glucoside;

the white colonies correspond to the strains which do not produce the abovementioned enzymes.

The results are presented in Table III below:

TABLE III

|  |  | 24 hours Coloration of the colonies | | | |
|---|---|---|---|---|---|
| Species | Medium | Colorless | Blue | Brown-blue | Brown |
| E. coli | V | 2 | — | — | — |
| (2 strains) | VI | 2 | — | — | — |
|  | VII | 1 | — | — | 1 |
| E. cloacae | V | 1— | — | — | — |
| (1 strain) | VI | — | 1 | — | — |
|  | VII | — | 1 | — | — |
| K. pneumoniae | V | 1 | — | — | — |
| (1 strain) | VI | — | 1 | — | — |
|  | VII | — | 1 | — | — |
| M. morganii | V | — | — | — | 2 |
| (2 strains) | VI | 2 | — | — | — |
|  | VII | — | — | — | 2 |
| P. mirabilis | V | — | — | — | 2 |
| (2 strains) | VI | 2 | — | — | — |
|  | VII | — | — | — | 2 |
| P. vulgaris | V | — | — | — | 2 |
| (2 strains) | VI | — | 2 | — | — |
|  | VII | — | — | 2 | — |
| E. faecalis | V | 1 | — | — | — |
| (1 strain) | VI | — | 1 | — | — |
|  | VII | — | 1 | — | — |
| S. saprophyticus | V | 1 | — | — | — |
| (1 strain) | VI | 1 | — | — | — |
|  | VII | 1 | — | — | — |

*: number of strains, "—" = 0

As emerges from Table III above, the method according to the invention allows detection of bacteria of the group Proteus, and does not interfere with the detection of the β-glucosidase colonies, including when they are mixed. Specifically, for the culture of the mixture of K. pneumoniae and of P. mirabilis, on Medium VII, the two types of colony are perfectly distinguished, one brown and the other blue. Moreover, if a bacterium simultaneously expresses the two enzymatic activities (β-glucosidase and deaminase), its effect is the formation of colonies of a color which results from a mixture of blue and brown, as is the case for a strain of P. vulgaris on Medium VII.

EXAMPLE 9

The method and compounds according to the invention are in particular perfectly suitable for isolating and for identifying urinary microorganisms. The Medium VII was developed for this use; it has the following composition:

| Heart-brain extract (bioMérieux) | 5 g/l |
|---|---|
| bio-Soyase (bioMérieux) | 5 g/l |
| Tris buffer (Sigma) | 1 g/l |
| Monopotassium phosphate (Merck) | 1 g/l |
| Ammoniacal iron citrate (Sigma) | 0.5 g/l |
| 4-O-Toluene-sulfonyl-L-tyrosine | 0.4 g/l |
| 5-Bromo-4-chloro-3-indolyl-β-D-Glucoside (Biosynth) | 0.06 g/l |
| 6-Chloro-3-indolyl-β-D-glucuronide (Biosynth) | 0.25 g/l |
| Methyl-β-D-glucuronide (Sigma) | 0.1 g/l |

The pH of the media was adjusted to approximately 7.2.

25 bacterial strains were cultured directly in Petri dishes, on this medium. The strains which originate from the applicant's collection, belong to the following species: E. coli (3 strains), Citrobacter diversus (2 strains), E. cloacae (2 strains), K. pneumoniae (2 strains), M. morganii (2 strains), P. mirabilis (3 strains), P. vulgaris (2 strains), E. faecalis (2 strains), Staphylococcus aureus (2 strains), S. saprophyticus. (3 strains), Candida albicans (2 strains). In addition, a mixture of one strain of E. coli, of one strain of K. pneumoniae and of one strain of P. mirabilis was also cultured in Petri dishes. The dishes were incubated at 37° C. for 48 hours. The colonies formed were examined visually, after 24 and 48 hours of incubation respectively, according to the following interpretations:

the brown colonies correspond to strains which produce a deaminase belonging a priori to the group Proteus (represented herein by the species: M. morganii, P. mirabilis, P. vulgaris);

the Tyrian purple colonies correspond to strains which produce a β-D-glucuronidase belonging a priori to the species E. coli;

the blue colonies correspond to strains which produce a β-D-glucosidase belonging a priori either to the Klebsiella/Enterobacter/Serratia group, or to the genus Enterococcus;

the white colonies correspond to the strains which do not produce the abovementioned enzymes; they thus belong to other species of bacteria or yeasts, which are therefore to be identified with the aid of the usual techniques.

The results are presented in Table IV below:

TABLE IV

| | | Coloration of the colonies | | | | | 48 hours Coloration of the colonies | | | | |
|---|---|---|---|---|---|---|---|---|---|---|---|
| Species | Medium | Colorless | Brown | Grey-green | Blue | Tyrian purple | Colorless | Brown | Grey-green | Blue | Tyrian purple |
| E. coli (3 strains) | VIII | — | — | — | — | 3 | — | — | — | — | 3 |
| C. diversus (2 strains) | VIII | — | — | — | 2 | — | — | — | — | 2 | — |

TABLE IV-continued

| | | Coloration of the colonies | | | | | 48 hours Coloration of the colonies | | | | |
|---|---|---|---|---|---|---|---|---|---|---|---|
| Species | Medium | Colorless | Brown | Grey-green | Blue | Tyrian purple | Colorless | Brown | Grey-green | Blue | Tyrian purple |
| *E. cloacae* (2 strains) | VIII | — | — | — | 2 | — | — | — | — | 2 | — |
| *K. pneumoniae* (2 strains) | VIII | — | — | — | 2 | — | — | — | — | 2 | — |
| *M. Marganii* (2 strains) | VIII | — | 2 | — | — | — | — | 2 | — | — | — |
| *P. mirabilis* (3 strains) | VIII | — | 3 | — | — | — | — | 3 | — | — | — |
| *P. vulgaris* (2 strains) | VIII | — | — | 2 | — | — | — | — | 2 | — | — |
| *E. faecalis* (2 strains) | VIII | — | — | — | 2 | — | — | — | — | 2 | — |
| *S. aureus* (2 strains) | VIII | 2 | — | — | — | — | 2 | — | — | — | — |
| *S. saprophyticus* (3 strains) | VIII | 2 | — | — | — | — | 2 | — | — | — | — |
| *C. albicans* (2 strains) | VIII | 2 | — | — | — | — | 2 | — | — | — | — |
| Multimicrobial mixture (3 strains) | VIII | — | 1 | — | 1 | 1 | — | 1 | — | 1 | 1 |

*: number of strains "—" = 0

As emerges from Table IV above, the method according to the invention allows detection of the principal urinary bacteria, including when they are mixed together. Specifically, on Medium VIII, it is possible to detect four different types of colony (colorless, Tyrian purple, blue and brown), even in the case of a multimicrobial culture. Such a medium is particularly useful since it makes it possible to detect, as soon as they are isolated, the vast majority of the urinary microorganisms, which, as a result, simplifies both the identification and the analysis of the most complex samples, and thus simultaneously provides a benefit to the quality of the analysis and to its cost.

What is claimed:

1. Method for detecting and identifying and/or quantifying a deaminase enzymatic activity of a microorganism, comprising:
    bringing an inoculum suspected of containing a microorganism with a deaminase activity into contact with a culture medium for microorganisms, and
    detecting and identifying and/or quantifying a deaminase enzymatic activity; wherein
        the culture medium comprises at least one detection agent for demonstrating a deaminase activity by forming a colored product with a revealing agent comprising a color or fluorescent indicator;
        said detection agent being an L-amino acid of following general formula (I):

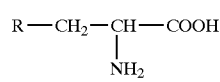
(I)

in which
        R represents an organic radical containing a cyclic ring, said cyclic ring being substituted with 1 to 3 substituents that are identical or different and each of which limits the diffusion in the culture medium of the α-keto acid produced by the deamination of the at least one detection agent, as compared to where each of said substituents is not present.

2. Method according to claim 1, characterized in that said 1 to 3 substituents are chosen from hydrophobic groups.

3. Method according to claim 2, wherein said 1 to 3 substituents are each selected from the group consisting of naphthalene-sulfonyl, tosyl-sulfonyl and mesitylene-sulfonyl.

4. Method according to claim 2, wherein each of said 2 or 3 substituents is a group that limits diffusion in hydrophilic medium.

5. Method according to claim 1, characterized in that the revealing agent is a cation salt.

6. Method according to claim 1, characterized in that the revealing agent is added to the culture medium at the same time as the detection agent.

7. Method according to claim 1, characterized in that the revealing agent is added to the culture medium after culturing the microorganisms.

8. Method according to claim 1, wherein the microorganisms which are detected and identified and/or quantified by enzymatic activity belong to the group Proteus.

9. Method according to claim 1, characterized in that at least one other detection agent for demonstrating, by forming a colored or fluorescent product, an enzymatic activity which is different from that demonstrated by the compound of general formula (I) is also added to said culture medium.

10. Method according to claim 1, wherein each of said 2 or 3 substituents is a group that associates with or binds to constituents of the cells of the microorganisms to limit diffusion.

11. The method of claim 1, wherein said 1 to 3 substituents are each selected from the group consisting of methyl, benzyl, carboxybenzoyl, dansyl, naphthalene, sulfonyl, tosyl, mesitylene, toluene, naphthalene-sulfonyl, toluene-sulfonyl, and N-ind-mesitylene-sulfonyl.

12. A compound having the general formula (I):

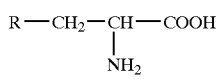

in which
R represents an organic radical containing a cyclic ring substituted with 2 or 3 substituents that are identical or different and each of which limits the diffusion in the culture medium of the α-keto acid produced by the deamination of the compound, as compared to where each of said substituents is not present,
wherein at least one of said 2 or 3 substituents is selected from the group consisting of naphthalene-sulfonyl, tosyl-sulfonyl and mesitylene-sulfonyl.

13. Compound according to claim 12, characterized in that said 2 or 3 substituents are chosen from hydrophobic groups.

14. Compound according to claim 13, characterized in that it is O-(2-naphthalen-sulfonyl)-tyrosine.

15. Compound according to claim 13, characterized in that it is 4-O-toluene-sulfonyl-L-tyrosine.

16. Compound according to claim 13, characterized in that it is N-toluene-sulfonyl-L-histidine.

17. Compound according to claim 13, wherein each of said 2 or 3 substituents is a group that limits diffusion in hydrophilic medium.

18. Compound according to claim 12, wherein said 2 or 3 substituents are each selected from the group consisting of naphthalene-sulfonyl, tosyl-sulfonyl and mesitylene-sulfonyl.

19. Compound according to claim 12, wherein each of said 2 or 3 substituents is a group that associates with or binds to constituents of the cells of the microorganisms to limit diffusion.

20. The compound of claim 12, wherein said 2 or 3 substituents are each selected from the group consisting of methyl, benzyl, carboxybenzoyl, dansyl, naphthalene, sulfonyl, tosyl, mesitylene, toluene, naphthalene-sulfonyl, toluene-sulfonyl, and N-ind-mesitylene-sulfonyl.

21. Method for preparing the compounds according to claim 12, comprising the following steps:
(a) formylation of the residue R,
(b) addition of a salt of each of said 2 or 3 substituents onto the residue R formylated according to (a),
(c) deformylation of the residue R substituted according to (b).

22. Culture medium for microorganisms, comprising, besides the ingredients required for culturing said microorganisms, at least one compound according to claim 12, as a detection agent.

23. Culture medium according to claim 22, characterized in that the weight concentration of the detection agent(s) is between 0.025 and 5 g/l of culture medium.

24. Culture medium according to claim 22, wherein weight concentration of the detection agent(s) is between 0.1 and 2 g/l.

25. Culture medium according to claim 22, further comprising a revealing agent comprising a color or fluorescent indicator.

26. Culture medium according to claim 22, characterized in that it is in a gelled form.

27. Culture medium according to claim 22, characterized in that it also comprises at least one other detection agent for demonstrating, by forming a colored or fluorescent product, an enzymatic activity which is different from that demonstrated by the compound of general formula (I).

28. Detection agent comprising:
(1) at least one compound having the general formula (I):

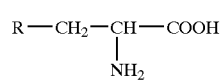

in which
R represents an organic radical containing a cyclic ring, substituted with 1 hydrophobic substituent limits the diffusion of the α-keto acid produced by the deamination of the compound, as compared to where each of said substituents is not present, or 1 substituent that binds to constituents of the cells of the microorganisms, and
(2) a revealing agent comprising a color or fluorescent indicator that produces a coloration or fluorescence with the at least one compound.

29. The detection agent of claim 28, wherein said substituent is selected from the group consisting of methyl, benzyl, carboxybenzoyl, dansyl, naphthalene, sulfonyl, tosyl, mesitylene, toluene, naphthalene-sulfonyl, toluene-sulfonyl, and N-ind-mesitylene-sulfonyl.

* * * * *